United States Patent [19]

Melnicoff et al.

[11] Patent Number: 5,256,532

[45] Date of Patent: Oct. 26, 1993

[54] METHODS, REAGENTS AND TEST KITS FOR DETERMINATION OF SUBPOPULATIONS OF BIOLOGICAL ENTITIES

[75] Inventors: Meryle J. Melnicoff, Cherry Hill, N.J.; Katharine A. Muirhead, West Chester; Paul K. Horan, Downingtown, both of Pa.

[73] Assignee: Zynaxis Technologies, Inc., Malvern, Pa.

[21] Appl. No.: 345,436

[22] Filed: May 1, 1989

Related U.S. Application Data

[63] Continuation-in-part of Ser. No. 189,192, May 2, 1988, abandoned.

[51] Int. Cl.$^5$ .............................................. C12Q 1/70
[52] U.S. Cl. ........................................ 435/5; 436/504; 436/518; 436/526; 436/536; 436/538; 436/71; 436/172; 436/173; 435/7.2; 435/7.24; 435/7.25; 435/7.32; 435/7.92
[58] Field of Search ............... 436/501, 503, 504, 518, 436/519, 526, 536, 538, 544, 545, 546, 71, 172, 173, 800, 829; 435/5, 7, 29, 21, 7.2, 7.25, 7.32, 7.92–7.95, 971

[56] References Cited

U.S. PATENT DOCUMENTS

| | | |
|---|---|---|
| 3,970,518 | 7/1976 | Giaever et al. |
| 4,157,323 | 6/1979 | Yen et al. |
| 4,219,411 | 8/1980 | Yen et al. |
| 4,230,685 | 10/1980 | Senyei et al. |
| 4,248,965 | 2/1981 | Mochida et al. ............ 436/518 |
| 4,284,412 | 8/1981 | Hansen et al. ............. 435/7.24 |
| 4,343,782 | 8/1982 | Shapiro et al. |
| 4,372,745 | 2/1983 | Mandel et al. |
| 4,486,530 | 12/1984 | David et al. ............... 435/7 |
| 4,532,203 | 7/1985 | Ullman et al. .............. 435/7.24 |
| 4,576,912 | 3/1986 | Yaverbaum et al. |
| 4,582,797 | 4/1986 | Trowbridge ................ 435/68 |
| 4,666,595 | 5/1987 | Graham et al. |
| 4,677,067 | 6/1987 | Schwartz et al. |
| 4,698,263 | 10/1987 | Wagner et al. |
| 4,708,933 | 11/1987 | Huang et al. ............... 435/7 |
| 4,710,472 | 12/1987 | Saur et al. |
| 4,717,676 | 1/1988 | Wagner et al. ............. 435/6 |
| 4,727,020 | 2/1988 | Recktenwald .............. 435/6 |
| 4,748,129 | 5/1988 | Chang et al. |
| 4,783,401 | 10/1988 | Horan et al. |
| 4,876,189 | 10/1989 | Schetters et al. ........... 435/7 |
| 4,978,625 | 12/1990 | Wagner et al. ............. 436/518 |

FOREIGN PATENT DOCUMENTS

| | | |
|---|---|---|
| 22948/88 | 4/1989 | Australia. |
| 2012934 | 9/1990 | Canada. |
| 2012939 | 9/1990 | Canada. |
| 60-017359 | 1/1985 | Japan. |
| 60-138464 | 7/1985 | Japan. |
| 60-138465 | 7/1985 | Japan. |
| 60-138466 | 7/1985 | Japan. |
| 60-159652 | 8/1985 | Japan. |

OTHER PUBLICATIONS

E. Menz et.al., Am. Biotech. Lab. (1986).
D. Monroe, Am. Biotech. Lab. 5: 10–19 (1987).
(List continued on next page.)

*Primary Examiner*—Esther L. Kepplinger
*Assistant Examiner*—Carol A. Spiegel
*Attorney, Agent, or Firm*—Dann, Dorfman, Herrell and Skillman

[57] ABSTRACT

Analytes, having a characteristic determinant that selectively interacts with a specific binding substance, are determined by coupling a reporter substance to the analyte, or to the specific binding substance, causing complex formation between the analyte and the specific binding substance in a test medium, separating the complexes thus formed from the test medium, and determining the presence or quantity of the analyte of interest by detecting the occurrence of the reporter substance in the complexes or the separated test medium. The determination is preferably performed on biomembrane-containing entities, such as cell subpopulations and/or subsets thereof, the reporter substance being stably associated with the lipid component of the biomembrane. Reagents and test kits are disclosed for performing the analyte determination.

49 Claims, 2 Drawing Sheets

OTHER PUBLICATIONS

H. Moscoso et.al., Clin. Chem. 34/5: 902-05 (1988).
R. Nargessi et.al., J. Immunol. Meth. 71:17-24 (1984).
S. Rattle et.al., Clin. Chem. 30/9: 1457-61 (1984).
F. Szoka et.al., Ann. Rev. Biophys. Bioeng. 9:467-508 (1980.
A. Truneh et.al., J. Immunol. Meth. 100:59-71 (1987).
C. Yeh et.al., J. Immunol. Meth. 43: 269-75 (1981).
J. Kemshead & J. Ugelstad, Molec. and Cellular Biochemistry 67:11-18 (1985).
A. Landay, et.al., Clin. Immunol. Immunopath. 52:48-60 (1989).
T. Lievestad et.al., Tissue Antigens 28: 46-52 (1986).
D. Lewinsohn et.al., J. Immunol. Meth. 110: 93-100 (1988).
P. Machy et.al., Proc.Nat.Acad.Sci. 79: 4148-52 (1982).
J. Berman et.al., J. Immunol. 138: 2100-03 (1987).
J. Brinchmann et.al., Clin.Exp.Immunol.71: 182-86 (1988).
J. Endl et.al., J. Immunol. Methods 102: 77-83 (1987).
V. Ghararossian et.al., Clin. Chem. 34/9: 1720-25 (1988).
R. Kamel et.al., Clin. Chem. 26/9: 1281-84 (1980).
J. Kemshead et.al., Br. J. Cancer 54: 771-78 (1986).
Butturini et al., Progress in Bone Marrow Transplantation, pp. 413-422 (1987).
Ngo, T. et al, Enzyme-Mediated Immunoassay, (Pleun Press New York 1985) pp. 472-473.
Calbiochem Biochemical/Immunochemical Catalog 1989, p. 53.
Oellerich, M, J. Clin. Chem. Clin. Biochem., vol. 22(12), pp. 895-904 (1984).

METHODS, REAGENTS AND TEST KITS FOR DETERMINATION OF SUBPOPULATIONS OF BIOLOGICAL ENTITIES

This application is a continuation-in-part of co-pending U.S. patent application Ser. No. 189,192, filed May 2, 1988 now abandoned and entitled "Compounds, Compositions and Methods for Binding Bio-Affecting Substances to Surface Membranes".

FIELD OF THE INVENTION

The present invention relates to biological testing and in particular to methods for determining the presence or quantity of a subpopulation of analytes, having at least one characteristic determinant, within a population including such analytes, and to reagents and test kits used in performing such methods. The methods, reagents and test kits of the invention facilitate screening of cells, viruses, and the like, by means of stably linking a detectable reporter substance to the lipid component of a biomembrane, separating the analyte of interest, e.g., via specific binding substances affixed to a solid phase, and detecting the reporter substance.

DESCRIPTION OF THE PRIOR ART

Determinations of components of blood or bone marrow, e.g., subpopulations of leukocytes, have become common clinical diagnostic tests due to the general availability of monoclonal antibodies selectively reactive with determinants of the discrete components. These determinations have proven useful for monitoring changes in immunodeficiency diseases, leukemias, lymphomas and transplant patients. See: A. Landay and K. Muirhead, J. Clin. Immunopathol., 52: 48-60 (1989). Immunofluorescence labeling followed by flow cytometric analysis is the established method for performing such determinations.

Flow cytometry has decided advantages over other commonly used cell marker analysis techniques, such as immunofluorescence microscopy, immunocytochemistry, and enzyme immunoassay. One significant advantage over bulk methods, e.g., fluorimetry or enzyme immunoassay, is the ability to simultaneously quantify multiple cellular subpopulations in one sample. Flow cytometry has several notable advantages over manual fluorescence microscopy. These include: (i) the ability of the instrument to rapidly score thousands of cells for positive or negative immunofluorescence, (ii) better reproducibility of results, (iii) permanent records of data, and (iv) greater sensitivity for detection of weakly fluorescing cells.

However, one distinct disadvantage of flow cytometry is that each sample must be run and analyzed individually. This disadvantage is particularly significant in a clinical laboratory which must process multiple patient specimens daily. The ability to quantitate cell subpopulations from multiple samples at once would substantially reduce the throughput time for this operation in the clinical or research laboratory.

One proposed method for analyzing multiple samples is enzyme-linked immunosorbent assay (ELISA). See: J. Endl. et al., J. Immunol. Meth., 102:77-83 (1987). This assay measures absorbance of multiple samples at one time using a 96-well microplate reader. The reporter system in this assay utilizes an enzyme, $\beta$-galactosidase, which is present in blood monocytes and neutrophils. Therefore, the blood specimen must be separated to remove interfering cells or cellular materials before performing this assay. Consequently, this technique is not well-suited to determination of cell subpopulations in whole blood. Moreover, because this assay measures absorbance of the reporter molecule, it is less sensitive than a fluorescent detection system.

In the practice of immunofluorescence labeling and other immunoassay techniques, it is common to label antibodies directly with fluorescent, enzymatic or radioisotopic reporters. The number of such reporters that may be bound to an antibody molecule without changing its immunoreactivity, however, is quite limited. Moreover, the covalent bonding of a fluorochrome or radioisotopic reporter to an antibody requires compatible reactive groups on each reactant, which imposes another practical limitation on this sort of labeling.

In order to avoid direct labelling of fluorescent reporters to antibodies for use in flow cytometry and fluorescence microscopy, it has been proposed to use reagents comprising antibodies attached to liposomes loaded with dye molecules entrapped in the aqueous phase inside the liposomes. The increased number of reporter molecules per antibody has been found to enhance signal amplification. Furthermore, encapsulation of the reporter within the liposome permits a wider range of reporter molecules to be used, including those that cannot be directly bound to antibody. See: A. Truneh et al., J. Immunol. Methods, 100:59-71 (1987) and references cited therein; and U.S. Pat. No. 4,372,745 to R. Mandle et al.

Similar reagents have been proposed for use in other diagnostic applications. The patent literature discloses immunoassays utilizing reagents in which a specific binding substance for an immunoreactive substance of interest is fixed on lipid membrane-containing microcapsules, having a hydrophilic marker encapsulated in the microcapsules. In performing such immunoassays, a test sample containing the immunoreactive substance of interest is mixed with the reagent and a source of complement, causing the marker to be released from the microcapsules, after which its presence or quantity is determined by appropriate analysis. See, for example, Japanese Patents 60159652-A and 60017359-A. According to the specific embodiments disclosed in these references, the microcapsules are liposomes which are fixed to the specific binding substance via covalent bonds. See also: Japanese Patents 60138464-A, 60138465-A and 60138466-A. An additional advantage of this method is the ability to measure bound reagent in the presence of unbound reagent. However, this method also has several disadvantages. First, complement is a labile reagent and false negatives may result in this method from failure of complement to properly lyse liposomes and release reporter Second, if the disclosed reagent were used to determine cell surface associated structures, complement could cause lysis of cells as well as liposomes, releasing substances which may interfere with measurement of some reporter molecules. Third, microenvironments within some test samples (e.g., low pH) may cause significant leakage and nonspecific release of some reporter molecules e.g., carboxyfluorescein. See: P. Machy et al., Proc. Nat. Acad. Sci. USA, 79:4818 (1982)).

Liposome reagents have also been proposed for use in determining soluble analytes, as described, for example, in U.S. Pat. Nos. 4,717,676 and 4,698,263.

Another way of overcoming the above-noted limitation of directly coupling fluorescent reporter to antibodies in fluoroimmunoassays is described in U.S. Pat. No. 4,576,912 to S. Yaverbaum et al. The immunoassay technique disclosed therein involves the use of a reagent, comprising a carrier bearing a plurality of closely-packed fluorophores, which is coupled to an immunological reactant competitive with the immunological reactant of interest for binding to a known quantity of complementary binding substance. The fluorophores are sufficiently closely packed as to exhibit self-quenching and the reagent is capable of undergoing chemical treatment to release the fluorophores. A test sample and the reagent are mixed with a solid phase bearing the complementary binding substance for the immunological reactant of interest. After the competitive-binding reaction occurs, the bound immunological reactants and unbound immunological reactants are separated. The carrier, in either or both separated portions, is then chemically treated, or lysed, to liberate the otherwise quenched, closely-packed fluorophores to greatly enhance the measured fluorescence. The fluorescence intensity of the liberated fluorophores is then compared to a standard of known concentration to determine the amount of immunological reactant in the sample. This immunoassay technique is not without certain drawbacks, however, in that the chemical reaction used to effect reporter release prior to detection is typically a time consuming enzymatic reaction.

Another method for detection of cell surface antigens or antibodies thereto measures agglutination of fluorochrome labeled erythrocytes. V. Ghazarossian et al., Clin. Chem., 34:1720-25 (1988); see also U.S. Pat. No. 4,748,129. This method has particular application for blood typing or the detection of antibodies to blood group antigens. Fluorochromes are used to label erythrocyte membranes and the presence of the antibodies or antigens is then determined from fluctuations in the fluorescence signal (detected by a fiber optic probe) due to agglutination of the erythrocytes. This system can produce only qualitative or, at best, semi-quantitative results as to the presence or absence of antigens or antibodies of interest. Erythrocytes are stained by adding the dyes in organic solvent to whole blood where the dyes partition between the cells and the plasma. The dyes used in this assay (e.g., 1,3,-bis[4-diethylamino-2-hydroxyphenyl]-2,4-dihydroxycyclobutene-diylium dihydroxide) transfer from the erythrocytes to plasma during the assay, with the cells losing as much as 40% of the dye during a 10 minute incubation at 37° C. When the assay is employed to measure the presence of antibodies in plasma, erythrocytes in the blood sample are removed by the addition of colloidal magnetite particles and exposure of the sample to a magnetic field.

In diagnostic testing, it is often desirable to sort out and separate for further analysis a cell subpopulation or subset of interest from a mixed cell population.

One cell separation technique uses magnetic particles and magnetic affinity separation. Various methods for sorting biological populations by magnetic affinity separation have been described in the patent literature and in a number of periodical scientific publications. See, for example, U.S. Pat. Nos. 3,970,518, 4,710,472, 4,677,067, 4,666,595, 4,230,685, 4,219,411, 4,157,323; see also, E. T. Menz, et al., Am. Biotech. Lab. (1986); J. S. Kemshead et al., Molec. Cell. Biochem., 67:11-18 (1985); T. Leivestad et al., Tissue Antigens, 28:46-52 (1986); and J. S. Berman et al., J. Immunol., 138:2100-03 (1987). In performing such methods, a receptor molecule (e.g., monoclonal antibody) is typically conjugated to the magnetic particles, and added to a test sample under conditions causing binding to a characteristic determinant on the analyte of interest, after which the test sample is exposed to a magnetic field. See, for example, the immunomagnetic separation technique described by Leivestad et al., supra. The magnetic particles and analyte affixed thereto can then be separated from the rest of the population.

The use of magnetic affinity separation has been reported in clinical diagnostic immunoassays for soluble analytes which utilize a radioisotope (see, for example, Rattle et al., Clin. Chem., 30:1457-61 (1984) or fluorescent molecules (see, for example, Moscoso et al., Clin. Chem., 34:902-05 (1988); R. D. Nargessi et al., J. Immunol. Meth., 71:17-24 (1984); and Kamel et al., Clin. Chem. 26:1281-84 (1980)) as the reporter substance. The use of this technology to separate certain subpopulations of lymphocytes from bone marrow cells prior to transplantation, to eliminate post-transplantation graft vs. host reaction, has also been reported. See A. Butturini et al., Prog. Bone Marrow Transpl. 413-22 (1987). Other reported uses of this technology include the separation of tumor cells (see: Kempshed et al., B. J. Cancer 54:771-78 (1986)) and the separation of lymphocyte subpopulations for subsequent functional evaluation (Berman et al., supra).

The application of magnetic affinity cell separation to the quantitation of lymphocyte subsets in blood has been reported. See J. Brinchmann, Clin. Exp. Immunol., 71:182-86 (1988). In this procedure, blood samples were incubated with superparamagnetic polymer microspheres coated with monoclonal antibodies specific for distinct lymphocyte subpopulations. The cells bound to the microspheres were isolated from the rest of the population by applying a magnetic field to the sample. The separated cells were then lysed to detach them from the microspheres, the microspheres and attached cell membranes were magnetically removed, and the resulting cell nuclei were stained and counted manually with a fluorescent microscope and hemacytometer. The number of nuclei counted corresponded to the number of cells in the sample in the subpopulation of interest. While this procedure may be used to enumerate the cells in a subpopulation of interest, manual enumeration of the cell nuclei is very time consuming and susceptible to technical error in sample loading of the hemacytometer and counting. Such a procedure would not be suitable for use in a clinical setting.

A need exists, therefore, for improved methods to determine analytes, particularly cell subpopulations. The characteristics of such improved methods should include: sensitivity comparable to or greater than methods heretofore available, ability to analyze multiple samples in a relatively brief time, and elimination of the need for expensive equipment and highly skilled personnel to perform the method.

SUMMARY OF THE INVENTION

According to one aspect of the invention, the determination of analyte having at least one characteristic determinant in a test sample suspected of containing such analyte, is performed by initially coupling the analyte of interest to a detectable reporter substance. The test sample is then contacted with a specific binding substance capable of interacting selectively with at least one characteristic determinant of the analyte of interest, under conditions causing complex formation between the analyte and the specific binding substance. Next, the complexes thus formed are separated from any free substance, so as to form two fractions. The occurrence of the reporter substance in one of the separated fractions is then detected. Ordinarily, the level of detected reporter substance is correlated to a predetermined standard to determine the presence or quantity of the analyte of interest within the test sample. This procedure is particularly useful for determining analytes which are biomembrane-containing entities, with the reporter substance being stably associated with the lipid content of the biomembrane. In a preferred embodiment of the invention, cell populations are analyzed, using the procedure just described, to determine the presence or quantity of a cell subpopulation of interest within the population.

In another aspect of the invention, analyte having at least one characteristic determinant is determined in a test sample by contacting analyte from the test sample with a reagent comprising a lipid-containing moiety, a specific binding moiety capable of selective interaction with the characteristic determinant of the analyte and a detectable reporter moiety which is stably associated with the lipid-containing moiety, under conditions causing binding of the reagent to the analyte. Thereafter, the occurrence of the detectable reporter substance bound to the analyte is detected.

Unlike some of the above-noted prior art analytical techniques, the methods of the present invention do not employ covalent coupling of reporter substances to a specific binding substance as a matter of choice. Rather, the reporter substance is preferably caused to become stably associated with the lipid component of the analyte or the lipid component of the reagent comprising the specific binding substance. By proceeding in this way, there is no appreciable leakage of the reporter substance so long as the integrity of the aforesaid lipid component is maintained, yet the reporter substance may readily be dissociated from the analyte or reagent, as the case may be, by treatment with a suitable extractant. The use of extractable reporter substances in the methods of this invention constitutes a distinct advantage over related prior art procedures wherein the reporter is not extractable. Extractable fluorochromes provide a particular advantage when used as the reporter substance, as fluorescence efficiency may be increased by extraction and concentration of the fluorescent reporter prior to fluorescence measurement. Extractability of the reporter substance has an added advantage in that detection of an extractable reporter can be accomplished using relatively simple and inexpensive analytical devices and techniques, e.g., fluorometry instead of flow cytometry.

According to further aspects of the invention, reagents and test kits are provided for performing the above described methods. The reagents have been briefly described above. The test kits may include various components depending on the nature of the analyte sought to be determined. Test kits may include the detectable reporter substance for binding to the analyte(s) of interest, having a characteristic determinant, and a specific binding agent that selectively interacts with the characteristic determinant of such analyte, e.g. for use in cell determinations. Other components included in the test kits may be one or more media for coupling the reporter substance to analyte, an extractant for the reporter substance, one or more standards for determining the presence or quantity of the analyte(s) of interest in the test sample, or instructions for the preparation of such standard(s), and, optionally, other accessories useful in carrying out the inventive methods.

Test kits for determining other analytes of interest having a characteristic determinant, such as allergens or autologous cells, may contain the above described reagent, comprising a lipid-containing moiety, a specific binding moiety that selectively interacts with the analyte determinant and a reporter moiety stably associated with the lipid-containing moiety.

The methods of the invention may be used as an adjunct to, and in certain instances as a replacement for the above noted analytical techniques currently applied in clinical laboratories, whose purpose is to screen for changes in cell frequency, e.g., flow cytometry. The methods described herein enable relatively rapid, simultaneous analysis of multiple biological samples with sensitivity comparable to that of the prior art. Moreover, the methods of the invention obviate the complex, expensive equipment and highly skilled personnel requirements of such prior art techniques.

Other advantages of the present invention will be apparent to those skilled in the art upon consideration of the drawing in conjunction with the detailed description of the invention presented below.

DETAILED DESCRIPTION OF THE INVENTION

The present invention provides methods for efficiently determining a broad range of analytes, which may be any constituent of a test sample or specimen whose presence or quantity may be determined by selective interaction with a specific binding substance. Thus, the term "analyte", as used herein, refers to a wide variety of substances of biological or medical interest which are measurable individually or as a group. Examples include cells, both eukaryotic (e.g., leukocytes, erythrocytes or fungi) and procaryotic (e.g., bacteria, protozoa or mycoplasma), viruses, cell components, molecules (e.g. proteins), and macromolecules (e.g. nucleic acids -RNA, DNA). These analytes may be determined as discrete entities or in the form of complexes or aggregates. Often it is desired to determine the presence or quantity of a subpopulation or subset of biomembrane-containing entities, i.e., analytes which contain naturally occurring lipid or phospholipid membranes, within a population. Examples include the determination of leukocytes within a population of blood cells, helper T lymphocytes within a population of lymphocytes, fetal cells within maternal circulation, virus-infected cells within a population of uninfected and infected cells, neoplastic cells within a population of normal and neoplastic cells, a protein of interest within a population of many different proteins or the like. Such determinations are accomplished using the methods of the invention, which rely on the selective interaction of the specific binding substance with at least one characteristic determinant of the subpopulation or subset of interest.

The term "determinant" is used herein in its broad sense to denote an element that identifies or determines the nature of something. When used in reference to any of the foregoing analytes, "determinant" means that portion of the analyte involved in and responsible for selective binding to the specific binding substance, the presence of which is required for selective binding to occur. Cell-associated determinants include, for example, components of the cell membrane, cytoplasm or nucleus. Among such cell-associated structures are membrane-bound proteins or glycoproteins, including cell surface antigens of either host cell or viral origin, histocompatibility antigens, or membrane receptors. One class of specific binding substances used to selectively interact with these determinants are antibodies capable of immunospecifically recognizing same. The term "antibody" as used herein includes immunoglobulins, monoclonal or polyclonal, and immunoreactive immunoglobulin fragments.

Further examples of characteristic determinants and their specific binding substances are: receptor—hormone, receptor—ligand, agonist—antagonist, RNA or DNA oligomers—complementary sequences, Fc receptor of mouse IgG—Protein A, avidin—biotin, and virus—receptor. Still other determinant-specific binding pair combinations that may be determined using the methods of the invention will be apparent to those skilled in the art.

The analyte of interest may be present in test samples or specimens of varying origin, including biological fluids such as whole blood, serum, plasma, urine, cerebrospinal fluid, amniotic fluid, lavage fluids and tissue extracts. In certain applications of the methods of the invention, the analyte may be adsorbed or immunologically captured onto a suitable solid support. Accordingly, it is within the scope of the present invention to detect, among other things, antigens, epitopes, antibodies, haptens or antigen-antibody complexes in biological fluids, autoantibodies bound to autologous cells in suspension and viral infections.

According to a preferred embodiment of the invention, analysis is performed on cell suspensions or populations including subpopulations and/or subsets expressing a characteristic integral membrane determinant to establish the total number of cells of interest within a sample cell suspension, or to determine the proportion of a cell subset within a cell subpopulation. Such cells of interest include cells of human or animal origin, cultured cells, as well as some single-celled organisms and virions. Cells of particular interest in current investigation include human and animal hemopoietic cells, including stem cells, progenitor cells of different lineages, cells at different stages of differentiation within a lineage, and mature forms of various lineages. Of particular interest in diagnostic, therapeutic and research applications are mammalian lymphocytes, including B cells, T cells and recognized T cell subsets, such as helper T cells, suppressor T cells and cytotoxic T cells. Different lineages of cells are characterized by expression of characteristic antigens or ligands. For example, B cells from mammalian blood samples express surface ligands distinct from those expressed by T cells from the same sample. Quantitation of one cell subset from the sample may be important in assessing certain pathological conditions. For example, individuals infected with human immunodeficiency virus (HIV) are tested for T helper cells bearing CD4 glycoprotein for purposes of determining the stage of disease and monitoring treatment. As another example, an abnormally large proportion of a single B cell clone in a patient's blood may be indicative of a leukemic condition. Cells from the same lineage at different stages of differentiation are also distinguishable by expression of characteristic antigens or ligands. For example, as a B lymphocyte develops from a stem cell to a pre-B cell and ultimately to a mature B cell, the cell membrane markers change in a predictable manner as the cell matures. A mature B cell expresses immunoglobulins as ligands on the cell membrane, whereas a pre-B cell expresses only cytoplasmic immunoglobulin heavy chains, which provides the basis for differential reactivity of these cell subsets, permitting subsequent determination. Differential expression of ligand can further provide a basis for assessing pathogenesis such as viral infection. Virally infected cells may express viral markers which are absent from uninfected cells within the cell population. These viral markers may be found intracellularly or on the cell membrane.

In analyzing cell populations for subpopulations or subsets of interest according to the above mentioned preferred embodiment, the cell population, suspended in a suitable biological or synthetic medium, is initially coupled to a detectable reporter substance. The expression "reporter substance" is used herein to refer to any substance whose detection or measurement, either directly or indirectly, by physical or chemical means, is indicative of the presence of the analyte of interest in the test sample. Examples of useful reporter substances include, but are not limited to the following: molecules or ions directly or indirectly detectable based on light absorbance, fluorescence, phosphorescence, or luminescence properties; molecules or ions detectable by their radioactive properties; and molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules. Fluorochromes, i.e., any of various fluorescent compounds used in biological staining to produce fluorescence in a specimen, are particularly useful as reporter substances in the practice of this invention. Representative fluorochromes are those selected from the group of cyanine, acridine, pyridine, anthraquinone, coumarin, quinoline, xanthene, phenoxazine, phenothiazine and hexatriene dyes and derivatives thereof.

One of the distinctive aspects of this invention involves the coupling of the lipid component of the aforesaid biomembrane-containing entities (including such entities associated with specific binding substances) to a unique class of reporter substances capable of stable association with such lipid component. The expression "stable association", used herein to describe the manner in which the reporter substance is linked to the lipid component of the biomembrane, is intended to mean that the affinity of the reporter substance for the lipid component of the membrane is greater than for the surrounding medium. The affinity of the below-described reporter substances for cell membranes is sufficiently strong that the reporter substance remains associated with the lipid component of the membrane even when exposed to conditions or agents having a tendency to cause leakage or loss of materials from membrane-containing microcapsules. See e.g., P. Machy et al., Proc. Nat. Acad. Sci., U.S.A., 79:4148 (1982); and Monroe, Amer. Biot. Lab, 5:10–19 (1987). Unlike previous cell labelling methods, see for example, V. Ghazarossian et al., Clin. Chem., 34:1720-25 (1988) and U.S. Pat. No. 4,748,129, this stable association between the reporter substance and the lipid component of a cell membrane is lost only when subject to conditions or agents which disrupt or destroy the integrity of the membrane's lipid component, such as by contact with detergents or lipid solvents which dissolve or disperse the lipid component.

On a quantitative basis, the expression "stably associated with" signifies that greater than 90% of the reporter substance initially linked to the lipid component of the cell membrane remains linked with the cell population or other biomembrane-containing entities throughout the course of the analysis (as detected by physical separation of cells from disassociated reporter substance), which is generally on the order of three hours.

Reporter substances capable of stable association with the lipid component of a biomembrane may comprise substances that are entirely hydrophobic in character, or that may include a moiety having at least one hydrophobic portion or domain serving to anchor the reporter molecule to such lipid component. In the latter instance, the hydrophobic portion of the reporter molecule should associate the molecule to lipid sufficiently to cause it to remain stably associated with the lipid, even in an agitated solution or disrupted cell suspension.

A particularly suitable group of reporter substances is represented by the formula:

(I)

wherein R and R₁ are the same or different and represent substituents independently selected from the group of hydrogen, alkyl, alkenyl, alkynyl, alkaryl or aralkyl, the hydrocarbon chains of which having from 1 to 30 carbon atoms, and being linear or branched, said substituents being unsubstituted or substituted with one or more non-polar functional groups, one of R or R₁ having at least 12 linear carbon atoms, and the sum of the linear carbon atoms in R and R₁ being at least 23;

X and X₁ may be the same or different and represent O, S, C(CH₃)₂ or Se;

Y represents a linking group selected from —CH=, —CH=CH—CH=, —CH=CH—CH=CH—CH=, or —CH=CH—CH=CH—CH=CH—CH=;

Z and Z₁ may be the same or different and represent substituents selected from the group H, alkyl, OH, NH₂, COOH, CONH₂, SO₃H, SO₂NH₂, NHNH₂, NCS, NCO, CONH-alkyl, CON-(alkyl)₂, NH-acyl, O-alkyl, NH-alkyl, or N(alkyl)₂, SH, S-alkyl, NO₂ or halogen, the alkyl groups comprising said Z substituents having from 1 to 3 carbon atoms; and A represents a biologically compatible anion.

A sub-group of useful reporter substances within the above-described group includes compounds of the formula:

(II)

wherein R and R₁ are the same or different and represent alkyl substituents, having from 1 to 30 carbon atoms, and being linear or branched, unsubstituted or substituted with halogen, one of R or R₁ having at least 12 linear carbon atoms and the sum of the linear atoms in R and R₁ being at least 23;

Z and Z₁ may be the same or different and represent substituents selected from the group H, or lower alkyl having from 1 to 3 carbon atoms; and A represents a biologically compatible anion.

Of the compounds represented by formula II, suitable reporter substances are 3-n-pentyl-3'-n-octadecyloxacarbocyanine iodide, 3-n-octyl-3'-n-octadecyloxacarbocyanine iodide, 3-n-propyl-3'-n-eicosanyloxacarbocyanine iodide, and 3-n-propyl-3'-n-docosanyloxacarbocyanine iodide.

Yet another subgroup of useful reporter substances within the above-described group includes compounds of the formula:

(III)

wherein R and R₁ are the same or different and represent alkyl substituents, having from 1 to 30 carbon atoms, and being linear or branched, unsubstituted or substituted with halogen, one of R or R₁ having at least 12 linear carbon atoms and the sum of the linear atoms in R and R₁ being at least 23;

Z and Z₁ may be the same or different and represent substituents selected from the group H, or lower alkyl having from 1 to 3 carbon atoms; and A represents a biologically compatible anion.

Among the compounds represented by formula III, suitable reporter substances include: 1,1'-di-n-octadecyl-3,3,3',3'-tetramethylindocarbocyanine perchlorate;

1-n-octadecyl-1'-n-pentyl-3,3,3',3'-tetramethylindocarbocyanine perchlorate; and 1-n-docosanyl-1'-n-propyl-3,3,3',3'-tetramethylindocarbocyanine iodide.

A further group of useful reporter substances includes compounds of the formula:

(IV)

wherein R represents a substituent selected from the group of alkyl, alkenyl, alkynyl, alkaryl or aralkyl, the hydrocarbon chain of which is linear or branched, said substituent being unsubstituted or substituted with one or more non-polar functional groups, and having at least 23 linear carbon atoms;

Z, $Z_1$ and $Z_2$ may be the same or different and represent substituents selected from the group H, akyl, OH, $NH_2$, COOH, $CONH_2$, $SO_3H$, $SO_2NH_2$, $NHNH_2$, NCS, NCO, CONH-alkyl, CON-(alkyl)$_2$, NH-acyl, O-alkyl, NH-alkyl, or N(alkyl)$_2$, SH, S-alkyl, $NO_2$, halogen, the alkyl groups comprising said Z substituents having from 1 to 3 carbon atoms; and A represents a biologically compatible anion.

Of the compounds represented by formula IV, a suitable reporter substance is 3,6-bis(dimethylamino)-10-n-hexacosanyl acridinium iodide. Other suitable fluorochrome compounds are 4-[4-didecylaminostyryl]-N-methyl-pyridinium iodide, N-3[3-Sulfopropyl]-4-[p-didecylaminostyryl]pyridinium inner salt and 2-[3-(1-n-docosanyl-benzoxazol-2-yliden)-1-propenyl]-6-iodo-1-n-tetradecylbenzothiazolium iodide.

As used in the preceding description of the reporter substance, the term "non-polar functional group" refers to substituents such as O-alkyl, S-alkyl, halogen, N(alkyl)$_2$, Se-alkyl, NO, CN, CO-alkyl, C=N-alkyl, —SiMe$_3$, O—SiMe$_3$, and the like.

Alternatively, the reporter substance may comprise a substantially hydrophobic chelate-metal complex, preferably wherein the chelate-metal complex comprises a metal ion selected from the transition metal series whose atomic number is from 21–29, the lanthanide series whose atomic number is 59–66 and the actinide series whose atomic number is 91, said complex being detectable by nuclear magnetic resonance or luminescence. The chelate-metal complex may also comprise a paramagnetic metal ion selected from the group of Gd, Cr, Dy, Ni, Cu, Fe and Co.

The reporter substance may also comprise a substantially hydrophobic substance incorporating a detectable radioisotope. The radioisotope incorporated into the reporter substance is preferably selected from the group of radioactive carbon, hydrogen, nitrogen, phosphorus, fluorine, chlorine, iodine, sulphur, selenium, cobalt and chromium.

The foregoing classes of hydrophobic reporter substances, are described in further detail, along with preparative procedures for specific compounds, in copending U.S. patent application Ser. No. 189,192, which is commonly assigned with the present application. The entire disclosure of Ser. No. 189,192 is incorporated in this specification by reference, as if set forth herein in full. The indocarbocyanine dyes are readily prepared following the general reaction scheme for oxacarbocyanine dyes set out in Ser. No. 189,192, substituting the appropriate indole derivatives for the benzoxazole derivatives used as starting materials in the reaction there described.

The reporter substances just described are characterized by having relatively long chain hydrocarbon substituents or "tails" that impart the requisite hydrophobicity/lipophilicity for stable association with the lipid-containing analytes or reagents. Once these compounds become bound to lipid, they cannot easily dissociate. Consequently, the reporter substance does not leak from the analytes or reagents and is not liable to be transferred to other biomolecules or cell-associated structures.

Details regarding the coupling of the above-described reporter substances to biomembrane-containing entities are provided in U.S. Pat. No. 4,783,401 to Horan et al., the entire disclosure of which is incorporated in this specification by reference, as if set forth herein in full. In general, coupling of the reporter substance to cells involves suspension of the cells in a suitable medium, e.g., 300 mOs per liter sucrose, at a concentration of $10^7$ to $10^9$ ml., followed by addition of the reporter substance to the cell suspension in an amount of about 1–20 uM and incubation of the suspension for about 5 minutes, at about 20°–30° C.

Determination of analytes according to the methods of the invention is accomplished by reason of the selective interaction between the analyte of interest and a specific binding substance. The specific binding substance used in the methods must exhibit selective recognition for the characteristic determinant of the analyte. The specific binding substance selected for a particular analysis will depend on the nature of the analyte being determined. In analyzing a cell population for a subpopulation and/or subset having a characteristic cell surface antigen, for example, the specific binding substance may be the complementary antibody that immunospecifically recognizes the antigen of interest. Based on such selective recognition, the specific binding substance is capaole of selective interaction and binding with the analyte of interest to form complexes or aggregates which are physically or chemically separable from the test medium and other components therein which are not of interest.

Specific binding substances are conveniently affixed to a solid phase to facilitate separation from the test medium. Techniques for immobilizing antibody on a solid support, e.g., polystyrene, nylon or agarose beads, are well known to those skilled in the art. Suitable techniques include cross-linking, covalent binding or physical adsorption. Alternatively, a non-solid phase, primary specific binding substance may be used in conjunction with a second or auxiliary specific binding substance which is capable of interacting selectively with the primary specific binding substance, and which is affixed to a solid phase. Representative primary and auxiliary specific binding substances useful for this purpose are: soluble murine antibody/Protein A affixed to a solid phase; soluble murine antibody/anti-mouse immunoglobulin raised in another species and affixed to a solid phase; biotinylated antibody/avidin affixed to a solid phase.

In a particularly preferred embodiment of the invention, the specific binding substance is affixed to a magnetic solid phase, which may comprise ferromagnetic, paramagnetic or diamagnetic material, thereby forming complexes or aggregates with the analyte of interest which are magnetically separable from the test medium. Suitable procedures for coupling specific binding substances to a magnetic solid phase, e.g., magnetite particles, are described in the literature. See, for example, E. Menz et al., Am. Biotech. Lab. (1986).

Figure 1:
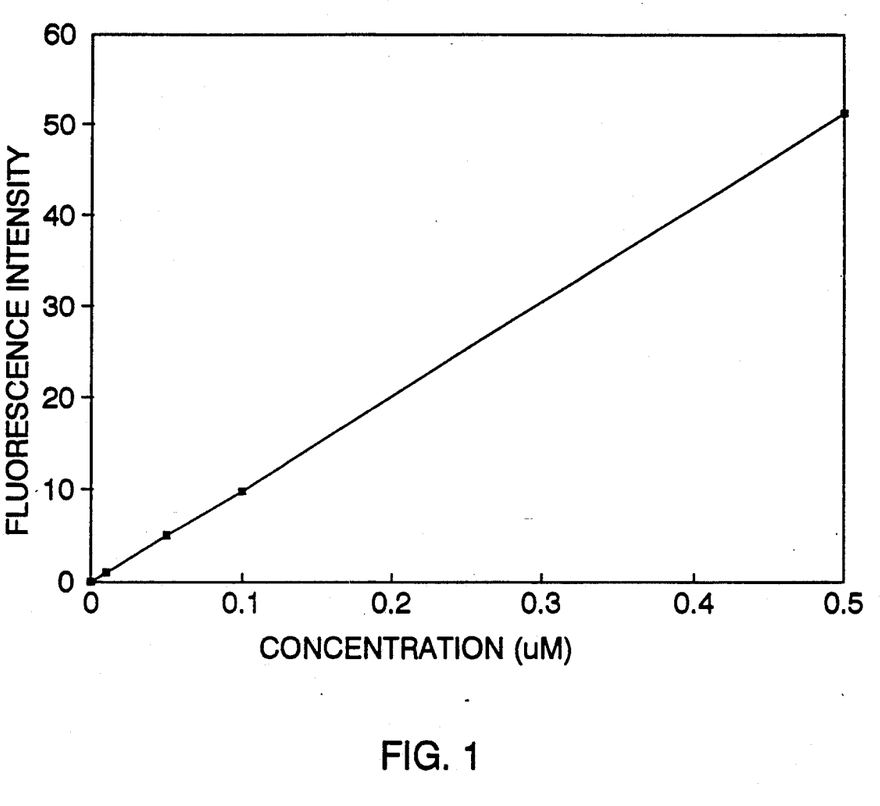
FIG. 1 is a standard curve showing fluorescence intensity as a function of reporter substance concentration for a series of solutions containing known concentrations of the fluorochrome 3-n-propyl-3'-n-docosanyloxacarbocyanine iodide (PDCI) as the reporter substance.

After separation of the analyte of interest from the test medium, detection of the reporter substance provides a basis for determining the occurrence of interaction between the analyte and the specific binding substance. The reporter substance may be detected in the separated analyte of interest, i.e., in the analyte/specific binding substance complexes, or in the test medium remaining after separation of the analyte of interest, which is substantially free of such complexes. The former procedure is preferred. The level of reporter substance detected in the separated analyte or in the remaining test medium may be correlated to a predetermined standard. Correlation to a standard may be employed whether the analyte determination is qualitative or quantitative. In a qualitative determination, the predetermined standard may be a negative control known to be free of the analyte of interest. Detection of the reporter substance in amounts appreciably higher than the background level of the negative control is indicative of the presence of the analyte of interest. In a quantitative determination, the level of detected reporter substance is compared to the level detected in e.g., one or more measured quantities of analyte, so as to establish the relative or absolute quantity of analyte of interest in the test sample. Quantitative determinations usually involve the preparation of a standard curve, containing increasing known quantities of reporter substance. These known quantities of reporter substances are plotted against the level of reporter substance detected. A typical standard curve for use in practicing the present invention is shown in FIG. 1. Based on the standard curve, the quantity of analyte in a test sample may be derived from the level of reporter substance detected therein.

Figure 2:
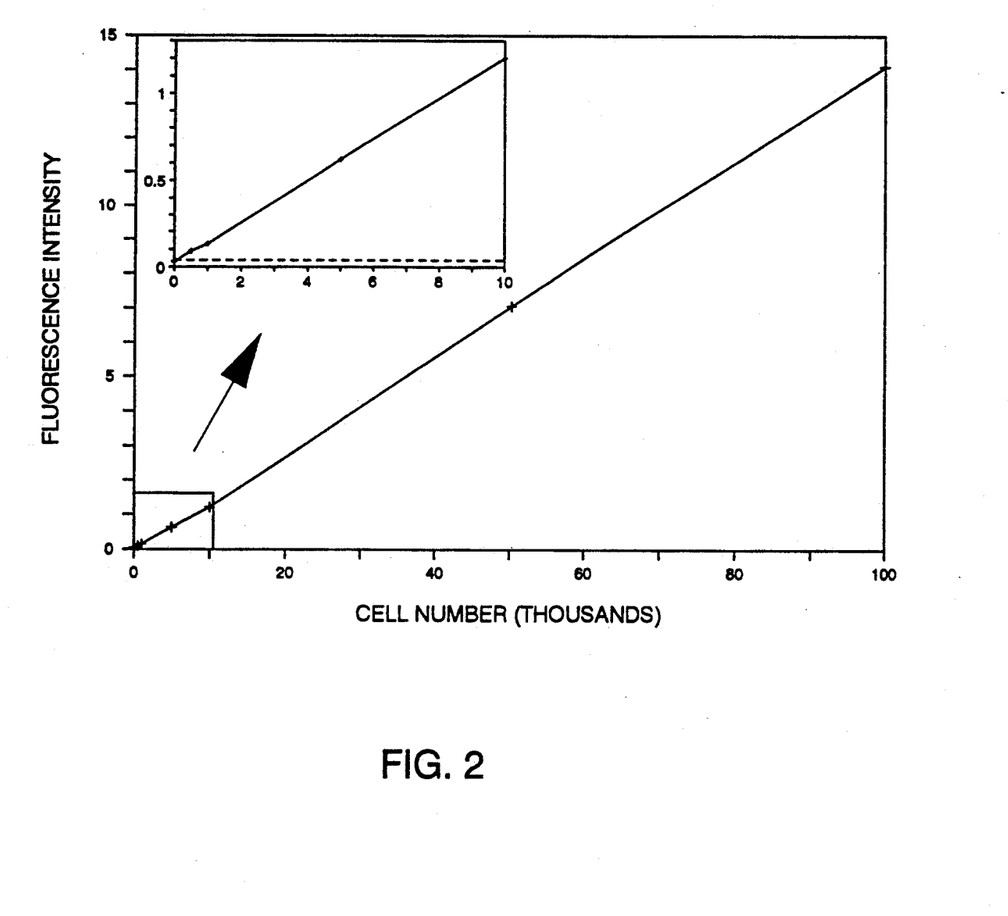
FIG. 2 is a graph representing the correlation between varying numbers of human mononuclear leukocytes coupled with 3-n-propyl-3'-n-docosanyloxacarbocyanine and fluorescence intensity of the reporter substance extracted from the same cells. The dashed line in FIG. 2 represents the average fluorescence intensity of an extract of the cell population which was not coupled to reporter.

The predetermined standard for quantitative determination of analyte may be in various forms. Representative examples include compositions containing a measured number of membrane-bounded entities coupled to a measured amount of the detectable reporter substance, or a measured amount of reporter substance extracted from such entities, as shown in FIG. 2. The membrane-bounded entities comprising the standard may be the same as the entities being determined, naturally occurring biomembrane-containing entities of a different species, e.g., animal cells, organelles or the like, or non-naturally occurring membrane-bounded entities, having synthetic membranes composed of lipids or phospholipids, such as liposomes or micelles. The synthetic membrane bounded entities may be prepared with the reporter substance stably associated with the membrane lipid, e.g., according to the procedure, described in copending U.S. patent application Ser. No. 238,958, filed Aug. 31, 1988, now abandoned, the entire disclosure of which is incorporated in the present specification by reference, as if set forth herein in full. Alternatively, in the case of liposomes, for example, the reporter substance may be included in the aqueous phase, encapsulated by the lipid bilayer, and later extracted by the action of a suitable lysing agent, as is known in the art. See, for example, Szoka et al., Ann. Rev. Biophys. Bioeng. 9:467 (1986).

The reporter substance may be detected in several ways. The presence of reporter substance coupled to cells in either of the above-mentioned separated portions of the test medium may be determined directly from measurement of the individual cells and solution using automated methodology. Alternatively, the reporter substance may be removed by solvent extraction from the other components of the cell complexes. Extraction of the reporter substance is desirable in order to obtain a homogeneous distribution of the reporter substance for accurate analysis. In many cases, the unit absorbance (e.g., extinction coefficient) or fluorescence (e.g., quantum yield) of the reporter substance is greater after extraction, thereby increasing the detection sensitivity of the reporter substance. Extraction of the reporter substance may also be desirable to avoid potential interference with the measurement due to cellular material. Among the suitable extractants which may be used to dissociate the above-described reporter substances from biomembranes are butanol, ethanol or aqueous detergent solutions, e.g. TRITON ™ X-100 surfactant.

The foregoing method of the invention may be applied in analyzing a subpopulation of cells, present within a cell population, to determine the proportional occurrence therein of at least one cell subset of interest. This method may be applied, by way of example and not by way of limitation, to the determination of: lymphocyte, monocyte, and neutrophil subsets of a leukocyte subpopulation in a whole blood cell population; T cells and B cells of a lymphocyte subpopulation in a leukocyte population; or helper T cells and suppressor T cells of a T lymphocyte subpopulation in a total lymphocyte population. In order to determine the proportional occurrence of a subset of cells in this way, it is necessary to determine the relative number of cells in the individual subsets of interest as well as the relative number of the individual subsets of interest within the same sample or a sample of equivalent volume and cell concentration.

In carrying out this determination, substantially all of the cells comprising the population suspected of containing the subpopulation of interest are coupled to a detectable reporter substance, such that the reporter substance is stably associated with the membrane of the cells. A first reagent is provided which incorporates at least one specific binding substance capable of selectively interacting with a characteristic determinant of the cell subpopulation. The first reagent may also comprise a mixture of specific binding substances, each binding to characteristic determinants of the individual subsets of interest within the cell subpopulation, so that substantially all cells of the subpopulation become bound to the first reagent. For example, a number of monoclonal antibodies which interact selectively with the characteristic antigens of a defined number of cell subsets may be incorporated into the first reagent. The first reagent is contacted with a first sample of the population under conditions causing binding of the first reagent to cells of the subpopulation, so as to form first complexes in the sample. Next, the complexes thus formed are separated from unbound cells in the first sample and the occurrence of reporter substance in the separated complexes is detected. This procedure establishes the relative or absolute number of cells within the cell subpopulation of interest.

Thereafter, a second sample of the cell population to which the detectable reporter substance has been coupled, as described above, having volume and cell concentration equivalent to the first sample, is contacted with a second reagent comprising one or more specific binding substances that selectively interacts with a characteristic determinant of a cell subset of interest, under conditions causing binding of the second reagent to such determinant, so as to form second complexes in the second sample. The second complexes are separated from unbound cells in the second sample and the occurrence of reporter substance in the second complexes is detected.

The proportion of the subset of interest in the cell subpopulation is determined by quantitating the amount of reporter substance associated with the second complexes relative to the amount of reporter substance associated with the first complexes. In general, the level of detected reporter substance in each subpopulation and/or individual cell subset of interest may be related to a predetermined standard, in the manner previously described, to determine the presence or quantity of the cell subpopulation and/or cell subset of interest in the sample undergoing analysis. This determination of proportional subsets of interest is conveniently performed using reagent affixed to a solid phase, which preferably comprises magnetic material to facilitate separation from the test medium, and an extractable reporter substance.

If the population contains additional cell subsets of interest, additional reagents may be prepared, each reagent comprising one or more specific binding substances that selectively interact with a characteristic determinant of one of the additional subsets of interest. The additional reagents are contacted with additional samples of the above-mentioned cell population, each sample once again being of equivalent volume and cell concentration to the first sample, under conditions causing the formation of additional complexes between the additional reagents and cell subsets of interest in the additional samples. Detection of the reporter substance in the complexes separated from each additional sample provides an indication of the proportional occurrence of the individual subsets of interest within each sample. Thus, the proportional occurrence determination of subsets in the additional samples is carried out in the same manner as the determination of the cell subset of interest in the second sample, described above.

As previously noted, analyte may be determined in accordance with this invention by a method in which the reporter substance is coupled with a specific binding substance, rather than with the analyte. Specifically, a reagent is used which comprises a lipid-containing moiety, a specific binding moiety capable of selective interaction with the characteristic determinant of the analyte and a detectable reporter moiety which is stably associated with the lipid-containing moiety. This method may be implemented on the basis of non-competitive binding interaction or competitive binding interaction between the analyte and its specific binding substance. The non-competitive binding procedure is conveniently performed by immobilizing analyte from the test sample, contacting the immobilized analyte with the reagent under conditions causing binding of the reagent to the analyte and determining the occurrence of the detectable reporter substance bound to the immobilized analyte. The parameters for practicing this method are essentially the same as those set forth above in relation to the earlier described method in which the reporter substance is coupled to the analyte. In the competitive binding procedure, the step of contacting the test sample with the specific binding substance includes adding to the test sample a known quantity of the analyte to be determined, thereby to effect competition between any analyte originally present in the test sample and the added analyte for complex formation with the specific binding substance. The presence or quantity of the analyte of interest in the test sample is determined in accordance with conventional competitive binding assay techniques.

This method is suitably used, for example, in the early determination of viral infection. In performing this determination, a reagent is prepared from biomembrane-containing entities bearing natural or induced receptors for viral determinants or viral-induced determinants in the host cell. The membrane of these entities is stably associated with one of the above-described reporter substances. The resultant reagent is then incubated with the infected cells. The infected cells bearing the reporter substance may be identified microscopically, or, if desired, the extent of infection may be determined by extracting and quantitating the reporter substance. Similarly, analyte from a biological sample, e.g., patient serum, may be immobilized on a solid support, and its presence or quantity determined by interaction with a reagent comprising analyte receptor-bearing cells, which are coupled to one of the above-mentioned reporter substances, and determining the level of receptor substance bound to the solid phase. This technique may be used, for example, in allergen testing, using IgE receptor-bearing cells or red blood cells linked to anti-human IgE, each being coupled to a reporter substance. Replacement of radiolabeled antibody, typically used in allergy testing, with a reagent of the invention coupled to an extractable fluorochrome, for example, would allay the concern of many clinicians about the use of radioactive reagents. In addition, autoantibodies bound to autologous cells may be identified using this method, by incubating autoantibody-bearing autologous cells with a reagent comprising IgE receptor-bearing cells coupled to a suitable reporter substance, isolating the resulting complexes via affinity separation and detecting reporter substance. This method may also be used in identifying and/or quantitating antigens or epitopes of interest, e.g., using antigen- or epitope-specific T or B cell clones.

In a variation of this embodiment of the invention, the presence or quantity of multiple analytes in a test sample is determinable, provided of course that each analyte has a characteristic determinant. For example, identification or quantitation of more than one cell subpopulation and/or cell subset within the same population can be achieved by means of this method. Such a cell population may contain or be suspected of containing two or more cell subsets, among other subsets, which for purposes of this discussion, are designated cell subset A and cell subset B, and which express determinant X and determinant Y, respectively, as characteristic markers. The determination of the presence and/or quantity of cells of cell subset A and cell subset B in the sample in clinical or experimental analysis can be efficiently done according to the latter method of the invention following a number of related protocols. Basically, the method involves preparing one specific binding substance that selectively interacts with cell subset A via a selective binding reaction with determinant X, thereby forming complexes between cell subset A and the one specific binding substance. Another specific binding substance is prepared that selectively interacts with determinant Y expressed by cell subset B.

In one protocol, discrete samples of the cell population of equivalent volume and cell concentration may be reacted serially with the one specific binding substance and then with the other specific binding substance. Following reaction and separation of complex from each reaction mixture, the reporter substance may be quantitated from each sample to provide an indication of the amount of cell subset A and the amount of cell subset B in the population. In this protocol, the reporter substance used in each of the reagents may be the same or different. Of course, additional specific binding substances may be prepared and used as needed for determination of other different cell subsets.

In an alternative protocol, the two specific binding substances may be reacted in the same sample of the population by adding and incubating both specific binding substances together to form discrete complexes within the sample. The resulting complexes are discrete due to the selective affinity of each specific binding substance for its respective different cell subset determinant. When the complexes are separated from the reaction, the total complexes will contain cell complexes formed by each of the selective reactions. In this protocol, the reporter substance coupled to the one specific binding substance must be distinguishable or separable from the reporter substance coupled to the other specific binding substance to permit distinct readings of the two cell subsets by detection of the two reporter substances. In this regard, the reporters may comprise substances having distinct spectral properties, by which is meant sufficiently differing excitation wave length(s), emission wavelength(s) or fluorescence lifetime(s), such that detection of the presence of one reporter substance is not compromised by the presence of any other reporter substance, i.e., the values determined for one are not significantly affected by the presence of the other. The use of such reporter substances permits individual measurement of each reporter independently of one or more other reporters present in the complexes. Alternatively, the one reporter may be physically separable from the other(s), e.g., by reason of its solubility.

The reagents used in the just described method are also within the scope of the present invention. Reagents of the invention may include specific binding substances that occur naturally on the surface of specific cells, such as hormone receptors, antibody on the surface of B lymphocytes or virus receptors on the surface of susceptible cells, e.g., helper T lymphocytes or monocytes having the surface glycoprotein CD4 are susceptible to HIV infection. Other specific binding substances which may be used in these reagents are substances expressed on cell surfaces after specific biological events that alter the cells. For example, interleukin-2 (IL-2) receptor is expressed at high levels on the surface of activated T lymphocytes, but at very low levels on the surface of resting lymphocytes. Similarly, viral antigens may be expressed on the surfaces of infected cells only. These are but two examples of receptor expression induced through physiologic activation. Other such examples will occur to those skilled in the art. Cells may also be transformed or transfected by recombinant DNA technology, to express specific binding substances on their surfaces. In each of these examples, the lipid containing moiety and the specific binding moiety occur naturally or are induced in a single entity, with the reporter substance being stably associated with the lipid moiety, i.e., the lipid component of the cell membrane.

The reagents of the invention may comprise cells, which are modified to incorporate specific binding substances, such as antibodies or antibody fragments that selectively interact with the characteristic determinant of the analyte of interest. Such modified cells can be prepared by linking to the cell surface a derivatized antibody or antibody fragment having at least one lipophilic hydrocarbon substituent. The hydrocarbon substituent must be of appropriate length to render the derivatized antibody or antibody fragment sufficiently non-polar as to have a surface membrane retention coefficient of at least about 90 during a 24 hour period in saline containing up to 10% serum, with the percent change in such coefficient during such period being less than 10%. Details of the procedure for preparing such derivatized antibodies or antibody fragments are provided in the aforementioned U.S. patent application Ser. No. 189,192. In addition, a hydrocarbon group of appropriate length and functionality may be embedded into the plasma membrane of the cells and thereafter coupled to the antibody or antibody fragment using procedures known in the art. Coupling of the resultant derivatized antibodies or antibody fragment to cells may be carried out in the manner described in the aforementioned U.S. Pat. No. 4,783,401.

The reporter moiety of the reagent may be any of the reporter substances described above in connection with the analyte determination methods of the invention.

The methods of the invention may be performed using conventional containers, including test tubes, multiwell plates, and the like. Detectors for accurately measuring the level of reporter substance in a test sample, such as a colorimeter, a spectrophotometer, a fluorospectrophotometer, a liquid scintillation counter or a gamma counter, are commercially available.

According to another aspect of the invention, premeasured quantities of the different reagents, together with the various accessories used in practicing the methods of the invention, including diluents, extractants, solid supports for immobilizing analyte, one or more standards, or instructions for the preparation thereof may be conveniently packaged in a test kit. The reagents in the test kit may take various forms. The reporter substance may be provided in the form of a solution, together with a suitable diluent for coupling reporter to cells. The reporter solution may be provided in a container suitable for performing the methods of the invention. Alternatively the reporter substance may be packaged dry, together with separate vials of diluent or solvent for addition to the reporter and/or other reagents in the course of carrying out the methods. The specific binding substance is preferably provided immobilized on a solid support, which may be suspended in a suitable buffer, lyophilized or dried.

The following examples are provided to describe the invention in further detail. These examples are intended to illustrate specific applications of the methods of the invention and should in no way be construed as limiting the invention. All solvent proportions are given by volume and all temperature in °C., unless otherwise indicated.

EXAMPLE 1

Relationship between fluorescence intensity of extracted fluorochrome substance and cell number Peripheral blood mononuclear cells were prepared from whole blood of a healthy donor by density gradient centrifugation. This preparation contains primarily lymphocytes and monocytes. The cells were coupled with 3-n-propyl-3'-n-docosanyloxacarbocyanine iodide (PDCI), using 10uM of this reporter and $1 \times 10^7$ cells/ml, with 300 mos per liter sucrose as the diluent. The resultant cells were incubated with reporter for 5 minutes at room temperature in a polypropylene tube. The coupling reaction was stopped by the addition of phosphate buffered saline (PBS) with 5% (w/v) bovine serum albumin (BSA). Cells were centrifuged at 350×g and the resulting pellet was washed twice with PBS with 1% BSA. Cell recovery after coupling with the reporter was 73% with 94% of the cells viable. Viability was determined by propidium iodide exclusion, according to the procedure described by C. Yeh et al., J. Immunol. Meth., 43:269-75 (1981).

Dilutions of the cell suspensions were prepared and aliquots corresponding to 500-100,000 cells were placed in wells of a 96 well culture plate. The plate was centrifuged at 350×g and the supenatants were decanted. Each pellet was resuspended in 250 $\mu$l of 1% TRITON TM X-100 (surfactant) in PBS and incubated for 5 minutes at room temperature. An aliquot of the cell extract (200 ul) was removed from each well and placed in a 96 well flat bottom reading plate made of black plastic.

Additionally, dilutions of PDCI in TRITON TM X-100 (surfactant) (0.005 uM to 1 uM of PDCI) were placed in another reading plate. This plate was used to establish a standard curve.

The fluorescence intensity of each sample in the reading plates was measured on a Fluoroskan TM II microplate reader (Flow Laboratories, Inc.) using 485 nm excitation filter and 538 nm emission filter.

As can be seen from FIG. 1, the fluorescence intensity of PDCI analyzed by the Fluoroscan II microplate reader is proportional to the concentration of PDCI. FIG. 2 shows that the fluorescence intensity of PDCI extracted from the cells is proportional to cell number. The data appearing in FIG. 2 further indicate that this analytical technique can detect less than 1000 or less PDCI-coupled cells after extraction.

EXAMPLE 2

Determination of the proportion of cells in subpopulations of leukocytes by immunoaffinity separation and extraction of fluorochrome reporter substance from cells coupled therewith Peripheral blood mononuclear cells were collected from healthy donors and stained with PDCI (2 uM concentration), as described above in Example 1. The resultant cells were suspended to a final concentration of $1 \times 10^7$/ml in wash buffer consisting of PBS with 1% BSA and 40 uM EDTA (ethylenediamine-tetraacetic acid).

Aliquots of PDCI-coupled cells were incubated with monoclonal antibodies (Mab) specific for lymphocyte subsets at a concentration of 20-40 Mab per $2 \times 10^6$ cells. The Mabs used were: anti-CD4, specific for helper T lymphocytes and monocytes; anti-CD8 recognizing suppressor/cytotoxic T lymphocytes; anti-CD19, specific for B lymphocytes, and a negative control Mab of the IgG$_1$ isotype. All Mabs were from AMAC, Inc. Cells were incubated with the Mabs for 30 minutes at 4°, washed twice in wash buffer, resuspended in 200 ul of wash buffer and placed in 4 ml polypropylene tubes. Then 50 ul of goat anti-mouse immunoglobulin conjugated to magnetic beads (Dynal Inc.) was added to each tube and the tubes were incubated for 30 minutes on a blood mixer (Robbins Scientific) at 4°.

The magnetic beads, and cells bound to the beads, were separated by adding 1 ml of wash buffer to the tube and then placing the reaction tube adjacent to a magnet for 1 minute. The supernatant, containing reaction fluid and unbound cells, was removed. The magnet was removed and 1 ml of wash buffer was added to the tube with gentle mixing to resuspend the resultant pellet. The magnet was reapplied as above and the supernatant was decanted. This procedure was repeated again. All of the supernatants from each reaction tube were pooled. After the last wash, the pooled supernatants were centrifuged and the cells were resuspended in 200 ul of wash buffer. The washed pellets from the magnetic separations were also resuspended in 200 ul wash buffer.

Aliquots (150ul) of each tube (those containing washed pellets and those containing cells from pooled supernatants of the magnetic separation) were transferred to wells of a 96 well plate. The plate was centrifuged and the supernatant decanted. Then the cells in each well were resuspended in 250 ul of 1% TRITON TM X-100 (surfactant) to extract the PDCI. The were analyzed on a Fluoroskan II plate reader as described above in Example I; this instrument performs fluorescence determination on up to ninety six (96) extracts in less than one minute. The percentage of Mab labeled cells was calculated as:

$$\frac{\text{Fluorescence intensity of pellet}}{\text{Fluorescence intensity of (pellet + supernatant)}} \times 100\%$$

Aliquots of cells from the same donor, which used for were not stained with PDCI, were immunofluorescence labeling. These samples were incubated with the same Mabs as above, then reacted with phycoerythrin conjugated goat anti-mouse immunoglobulin (Biomeda, Corp.). The cells were analyzed by flow immunofluorescence labeled cytometry, which is a method commonly used heretofore for this determination. Flow cytometry typically requires about one minute per fluorescence determination. The percentage of Mab labeled cells was calculated as:

TABLE I

Number of immunofluorescence positive
mononuclear cells × 100%
Total number of mononuclear cells counted The results of these determinations were:

| | Specimen 1 | | Specimen 2 | |
|---|---|---|---|---|
| Mab | Magnetic Separation | Flow Cytometry | Magnetic Separation | Flow Cytometry |
| Anti-CD4 | 64.0% | 63.7% | 51.7% | 47.2% |
| Anti-CD8 | 21.6% | 24.8% | 20.9% | 19.6% |
| Anti-CD19 | 12.2% | 6.0% | 7.5% | 5.8% |
| IgG1 control | 4.6% | 2.7% | 5.6% | 1.6% |

These results show that the proportion of cell subsets in a population expressing characteristic antigens can be determined by the method of the invention and that the results obtained by this method are comparable to those obtained by the conventional flow cytometric analysis and that for large numbers of fluorescence determinations, the method of the invention requires significantly less analysis time than the conventional method.

While certain embodiments of the present invention have been described and exemplified above, various other embodiments will be apparent to those skilled in the art from the foregoing disclosure. For example, antigen-specific cells involved in cell-mediated immunity may be determined utilizing the present invention. This determination is performed by coupling all immune cells in a test sample with one of the above-described reporter substances capable of stable association with the lipid component of the membranes of the immune cells, incubating the cells bearing the reporter substance with the antigen of interest bound to a solid support, separating unbound cells, extracting the reporter substance and determining the presence or quantity of antigen-specific cells bound. In addition to identification of specific immune cell subsets, the present invention may be used for making similar determinations in any other system where a panel of monoclonal antibodies is available, e.g., identification of bacterial, fungal, viral and parasitic analytes.

Moreover, while analyte determinations according to the preferred embodiment of this invention involve coupling the detectable reporter substance to analyte with the aid of stable association between the reporter substance and a lipid component of the analyte, this procedure has considerably broader applications. It should be understood, in this regard, that the same basic procedure may be applied in determinations of a wide range of analytes, using various other means to achieve reporter substance-analyte coupling, including chemical, physical or physico-chemical binding, e.g., covalent bonds, hydrogen bonds, polar attraction, van der Walls' attraction or adsorption, such as biospecific adsorption. Thus, it is contemplated that the methods described herein may be used for determination of substantially lipid-free analytes. Such methods are included within the scope of the present invention.

The present invention is, therefore, not limited to the particular embodiments described and exemplified, but is capable of considerable variation and modification without departure from the scope of the appended claims.

What is claimed is:

1. A method for determining the presence or quantity of analyte selected from the group consisting of eucaryotic cells, procaryotic cells and viruses, having lipid-containing membranes and at least one characteristic determinant, in a test sample suspected of containing said analyte, comprising the steps of:
   (i) coupling a detectable reproter substance non-selectively with said analyte in said test sample, said detectable reporter substance having a lipophilic moiety, which stably associates with said lip-containing membrane of said analyte;
   (ii) contacting said test sample with a specific binding substance which binds specifically to said at least one characteristic determinant of said analyte, under conditions causing complex formation between said analyte and said specific binding substance;
   (iii) after said coupling step and said contacting step, separating said test sample into a portion containing said complex and a portion substantially free of said complexes; and
   (iv) detecting the occurrence of said reporter substance in one of said separated portions to provide an indication of the presence or quantity of said analyte having said at least one characterstic determinant in said test sample.

2. A method according to claim 1, which also includes the step of relating the level of detected reporter substance to a predetermined standard to determine the presence or quantity of said analyte in said test sample.

3. A method according to claim 2, wherein the level of detected reporter substance is related to a standard containing a predetermined quantity of said reporter substance, thereby to quantiatively determine the analyte having said at least one characteristic determinant in said test sample.

4. A method according to claim 1, wherein the occurrence of said detectable reporter substance is detected in said complex-containing portion.

5. A method, according to claim 1, wherein said contacting step comprises contacting said test sample with said specific binding substance affixed to a solid phase.

6. A method according to claim 5, wherein the solid phase to which the specific binding substance is affixed comprises magnetic material, and said solid phase bearing said complex is magnetically separated from said complex-free portion.

7. A method according to claim 1, wherein said test sample is contacted with at least one antibody as said specific binding substance.

8. A method according to claim 7, wherein the said at least one antibody contacted with said test sample is affixed to a solid phase.

9. A method according to claim 7, wherein the said at least one antibody contacted with said test sample is a monoclonal antibody.

10. A method according to claim 1, wherein said contacting steps comprises contacting the test sample with a first specific binding substance which binds specifically to said at least one characteristic determinant of said analyte, and with second specific binding substance which binds specifically to said first specific binding substance, said second specific binding substance being affixed to a solid phase.

11. A method according to claim 10, wherein said test sample is contacted with a first antibody as the first specific binding substance and with a second antibody as the second specific binding substance.

12. A method according to claim 1, wherein said detectable reporter substance is extractably coupled to said analyte in said coupling step and said reporter substance is extracted therefrom prior to detection thereof.

13. A method according to claim 1, wherein the detectable reporter substance coupled to said analyte is selected from the group consisting of molecules or ions directly or indirectly detectable based on light absorbance, fluorescence, phosphorescence, or luminescence properties; molecules or ions detectable by their radioactive properties; and molecules or ions detectable by their nuclear magnetic resonance or paramagnetic properties.

14. A method for analyzing a population of cells with lipid-containing membranes to determine the presence or quantity of a subpopulation of said cells having at least one characteristic antigen, within said population, comprising:
   (i) coupling said cells of said population nonselectively to an extractable reporter substance, said extractable reporter substance having a lipophilic moiety, whereby said lipophilic moiety of said extractable reporter substance stably associates with said lipid-containing membranes of said cells;
   (ii) contacting said cell population with an antibody which binds specifically to said at least one characteristic antigen of said subpopulation of cells, under conditions causing binding of said antibody to said antigen, said antibody being affixed to magnetic particles;

(iii) magnetically separating said magnetic particles bearing said subpopulation of cells from said population;

(iv) extracting said reporter substance from said separated subpopulation of cells or from the population remaining after separation of said subpopulation; and (v) detecting the level of extracted reporter substance in said separated subpopulation of cells, or in the population remaining after separation of said subpopulation to provide an indication of the presence or quantity of the subpopulation of cells having said characteristic antigen within said population.

15. A method according to claim 14, which also includes the step of relating the level of detected reporter substance to a pre-determined standard to determine the presence or quantity of said subpopulation within said population.

16. A method according to claim 15, wherein the level of detected reporter substance is related to a standard containing a predetermined quantity of said reporter substance, thereby to determine the number of cells having said at least one characteristic antigen within said population.

17. A method according to claim 14, wherein the extractable substance coupled to said cells is selected from the group consisting of molecules or ions directly or indirectly detectable based on light absorbance, fluorescence, phosphorescence, or luminescence properties; molecules or ions detectable by their radioactive properties; and molecules or ions detectable by their nuclear magnetic resonance or paramagnetic properties.

18. A method according to claim 14, wherein said cells are coupled to a fluorochrome as the extractable reporter substance.

19. A method according to claim 14, wherein said population comprises cells selected from the group consisting of leukocytes, erythrocytes and mixtures thereof.

20. A method according to claim 14, wherein said population comprises hemopoietic cells and said subpopulation of cells is selected from the group consisting of hemopoietic cells of pre-determined lineage, homopoietic cells of pre-determined function or homopoietic cells of pre-determined stage of differentiation.

21. A method for analyzing a population of cells with lipid-containing membranes to determine the presence or quantity of a subpopulation of said cells having at least one characteristic antigen, within said population, comprising:

(i) coupling said cells of said population non-selectively to an extractable reporter substance said extractable reporter substance having a lipophilic moiety, whereby said lipophilic moiety of said extractable reporter substance stably associates with said lipid-containing membranes of said cells;

(ii) contacting said cell population with (a) an antibody which binds specifically to said at least one characteristic antigen of said subpopulation of cells and (b) a specific binding substance which binds specifically with said antibody, said specific binding substance being affixed to a solid phase;

(iii) separating from said population the solid phase bearing said subpopulation of cells;

(iv) extracting said extractable reporter substance from said separated subpopulation of cells or from the population remaining after separation of said subpopulation; and (v) detecting the level of extracted reporter substance in said separated subpopulation of cells, or in the population remaining after separation of said subpopulation to provide an indication of the presence or quantity of the subpopulation of cells having said characteristic antigen within said population.

22. A method according to claim 21, which also includes the step of relating the level of detected reporter substance to a pre-determined standard to determine the presence or quantity of said subpopulation within said population.

23. A method according to claim 21, wherein the extractable reporter substance coupled to said cells is selected from the group consisting of molecules or ions directly or indirectly detectable based on light absorbance, fluorescence, phosphorescence, or luminescence properties; molecules or ions detectable by their radioactive properties; and molecules or ions detectable by their nuclear magnetic resonance or paramagnetic properties.

24. A method according to claim 21, wherein said cells are coupled to a fluorochrome as the extractable reporter substance.

25. A method for analyzing a subpopulation of cells, having at least one characteristic determinant, present within a population of cells with lipid-containing membranes, said subpopulation of cells including individual subsets of interest, each said subset having at least one characteristic determinant, to determine the proportion of at least one subset of said cell subpopulation, comprising:

(i) non-selectively coupling substantially all of said cells of said population to a detectable reporter substance said detectable reporter substance having a lipophilic moiety, whereby said detectable reporter substance stably associates with said lipid-containing membranes of said cells;

(ii) contacting a first sample of said cell population from step (i) with a firs reagent comprising at least one specific binding substance which binds specifically to said at least one characteristic determinant of said cell subpopulation, under conditions causing binding of said first reagent to said cells of said subpopulation, thereby forming first complexes in said first sample;

(iii) separating said first complexes in said first sample from unbound cells in said first samples;

(iv) detecting the occurrence of said reporter substance in said first complexes;

(v) contacting a second sample of said cell population from step (i), of equivalent volume and cell concentration to said first sample, with a second reagent comprising a specific binding substance capable of selectively interacting with said at least one characteristic determinant of said at least one subset of interest in said subpopulation, under conditions causing binding of said second reagent to said at least one characteristic determinant, thereby forming second complexes in said second sample;

(vi) separating said second complexes in said second sample from unbound cells in said second sample;

(vii) detecting the occurrence of a reporter substance in said second complexes; and (viii) determining the proportion of said at least one subset of interest in said cell subpopulation by quantitating the amount of said reporter substance stably associated with said second complexes relative to the amount of said reporter substance stably associated with said first complexes.

26. A method according to claim 25, which includes:
(ix) contacting one or more additional samples of said cell population from step (i), each sample being of equivalent volume and cell concentration to said first sample, with one or more additional reagent, each said additional reagent comprising a specific binding substance which binds specifically to at least one characteristic determinant of one or more additional subset of interest respectively, under conditions causing binding of each additional reagent to each said subset, thereby forming additional complexes in said additional samples;
(x) separating each said additional complexes in said each additional sample from unbound cells in each said additional sample;
(xi) detecting the occurrence of said reporter substance in each said additional complexes; and
(xii) determining the proportion of each said additional subsets in said cell subpopulation by quantitating the amount of said reporter substance stably associated with each said additional complex relative to the amount of said reporter substance stably associated with said first complexes.

27. A method according to claim 25, wherein said first reagent comprises a mixture of specific binding substances, each said binding substance being capable of specifically binding to characteristic determinants of individual subsets of interest comprising said subpopulation, wehreby substantially all cells of said subpopulation are bound to said binding substances.

28. A method according to claim 25 or 26, which also includes the step of relating the level of detected reported substance to a predetermined standard to determine the presence or quantity of said subset within said subpopulation.

29. A method according to claim 26, wherein said specific binding substances of said first reagent, said second reagent and said one or more additional reagent being affixed to a solid phase.

30. A method according to claim 26, wherein said specific binding substances of said first reagent, said second reagent and said one or more additional reagent being affixed to magnetic particles, and said first complexes, said second complexes and said additional complexes bearing said subpopulations of interest are magnetically separated from said samples.

31. A method according to claim 26, wherein said specific binding substances of said first reagent, said second reagent and said one or more additional reagent comprise at least one antibody.

32. A method according to claim 26, wherein said specific binding substances of said first reagent, said second reagent and said one or more additional reagent comprise at least one monoclonal antibody.

33. A method according to claim 25 or 26, wherein said detectable reporter substance is extractably coupled to said cells and said reporter substance is extracted from said cells prior to detection thereof.

34. A method according to claim 25 or 26, wherein the reporter substance coupled to said cells is selected from the group consisting of molecules or ions directly or indirectly detectable based on light absorbance, fluorescence, phosphorescence, or luminescence properties; molecules or ions detectable by their radioactive properties; and molecules or ions detectable by their nuclear magnetic resonance or paramagnetic properties.

35. A method according to claim 25 or 26, wherein said detectable reporter substance coupled to said cells comprises a fluorochrome.

36. A method according to claim 25 which also includes before said separating step (iii), contacting said first sample with an auxiliary specific binding substance which binds specifically to said first reagent, said auxiliary specific binding substance being affixed to a solid phase.

37. A method according to claim 25, which also includes before said separating step (iii) contacting said second sample with an auxiliary specific binding substance which binds specifically to said second reagent, said auxiliary specific binding substance being affixed to a solid phase.

38. A method according to claim 26, which also includes before said separating step (vi) contacting at least one of said additional samples with an auxiliary specific binding substance which binds specifically to the additional reagent with which said additional sample is contacted, said auxiliary specific binding substance being affixed to a solid phase.

39. A method according to claim 36, 37 or 38, wherein said first sample, said second sample or said at least one additional sample are contacted with an antibody as the auxiliary specific binding substance.

40. A method according to claim 39, wherein the antibody contacted with said first sample, said second sample and said at least one additional sample is a monoclonal antibody.

41. A method for analyzing a population of cells with lipid-containing membranes to determine the presence or quantity of a subpopulation of said cells, having a characteristic determinant, within said population, comprising:
(i) coupling said cells of said population non-selectively to an extractable reporter substance, said extractable reporter substance having a lipophilic moiety, whereby said lipophilic moiety of said extractable reporter substance stably associates with said lipid-containing membranes of said cells;
(ii) contacting said cell population with a specific binding substance which binds specifically to said determinant under conditions causing binding of said specific binding substance to said determinant, said specific binding substance being affixed to a solid phase;
(iii) separating said solid phase, bearing said subpopulation, from said population;
(iv) extracting said reporter substance from said separated subpopulation of cells; and
(v) detecting the level of extracted reporter substance to provide an indication of the presence or quantity of the subpopulation of cells having said characteristic determinant within said population.

42. A method according to claim 41, which also includes the step of relating the level of detected reporter substance to a pre-determined standard to determine the presence or quantity of said subpopulation within said population.

43. A method according to claim 41, wherein the reporter substance coupled to said analyte is selected from the group consisting of molecules or ions directly or indirectly detectable based on light absorbance, fluorescence, phosphorescence, or luminescence properties; molecules or ions detectable by their radioactive properties; and molecules or ions detectable by their nuclear magnetic resonance or paramagnetic properties.

44. A method according to claim 41, wherein said cells are coupled to an extractable fluorochrome as the reporter substance.

45. A method according to claim 41, wherein said subpopulation has at least one antigen as said at least one characteristic determinant and said cell population is contacted with an antibody to said antigen, as the specific binding substance.

46. A method according to claim 45, wherein the antibody contacted with said cell population is a monoclonal antibody.

47. A method for determining the presence or quantity of a subpopulation of biological entities selected from the group consisting of eucaryotic cells, procaryotic cells and viruses, and having at least one characteristic determinant, within a population of said entities in a test sample, comprising:

(i) coupling a detectable reporter substance nonselectively to said population of biological entities;

(ii) contacting said biological entities in said test sample with a specific binding substance which binds specifically to said at least one characteristic determinant of said subpopulation of biological entities, under conditions causing binding of said binding substance to said at least one characteristic determinant;

(iii) separating said specific binding substance bearing said subpopulation of biological entities, from said population; and (iv) simultaneously detecting the occurrence of said detectable reporter substance in a plurality of said biological entities in said separated subpopulation of biological entities in said test sample or in a plurality of said biological entities in said population of said entities remaining in said test sample after separation of said subpopulation, thereby to provide an indication determinative of the presence or quantity of said subpopulation of biological entities having said at least one characteristic determinant within said population of biological entities having said at least one characteristic determinant within said population.

48. A method according to claim 47, which also includes the step of relating the level of detected reporter substance to a predetermined standard to determine the presence or quantity of said subpopulation within said population.

49. A method according to claim 47, wherein the level of detected reporter substance is related to a standard containing a predetermined quantity of said reporter substance, thereby to determine the number of said biological entities having said characteristic determinant within said population.

* * * * *